United States Patent [19]

Birnboim

[11] 4,407,942
[45] Oct. 4, 1983

[54] FLUORESCENT DETECTION OF DNA DAMAGE

[75] Inventor: Hyman C. Birnboim, Deep River, Canada

[73] Assignee: Atomic Energy of Canada Limited, Ottawa, Canada

[21] Appl. No.: 229,539

[22] Filed: Jan. 29, 1981

[51] Int. Cl.$^3$ .......................... C12Q 1/68; C12Q 1/29
[52] U.S. Cl. .......................................... 435/6; 435/29; 422/61; 436/63; 436/94
[58] Field of Search .................... 435/4, 6, 7, 29, 172; 23/230 B; 422/61; 424/7, 8; 436/63, 94

[56] References Cited

U.S. PATENT DOCUMENTS

| 3,798,131 | 3/1974 | Rounds et al. | 435/6 |
|---|---|---|---|
| 3,899,297 | 8/1975 | Hirschfeld | 435/6 |
| 4,257,774 | 3/1981 | Richardson et al. | 435/6 |
| 4,345,027 | 8/1982 | Dolbeare | 435/6 |

FOREIGN PATENT DOCUMENTS 649751  4/1979  U.S.S.R. ................................ 435/6

OTHER PUBLICATIONS

Kanter et al., "A Hydroxylapatite Batch Assay for Quantitation of Cellular DNA Damage", *Anal. Biochem.*, vol. 97, No. 1 (1979), pp. 77–84.
Erickson et al., "Measurement of DNA Damage in Unlabelled Mammalian on Cells Analyzed by Akaline Elution and a Fluorometric DNA Assay", *Anal. Biochem.*, vol. 106, No. 1 (1980), pp. 169–174.
Kohn et al., "Fractionation of DNA from Mammalian Cells by Akaline Elution", *Biochem.*, vol. 15, (1976), pp. 4629–4637.
Taylor, "A Rapid Single Step Staining Technique for DNA Analysis by Flow Microfluorimetry", *J. Histochem. Cytochem.*, vol. 28, No. 9, (1980), pp. 1021–1024.

*Primary Examiner*—Thomas G. Wiseman
*Attorney, Agent, or Firm*—Alan A. Thomson

[57] ABSTRACT

A sensitive method for detecting damage of DNA, e.g. resulting from exposure of living cells or whole organisms to low doses of radiation or chemicals, is described comprising: partial lysis of exposed cells to access the DNA; alkaline denaturing the DNA; after a selected interval stopping the denaturation by lowering the pH to a selected value; rendering the lysate homogeneous; adding an appropriate fluorescent dye which interacts preferentially with double-stranded DNA and measuring the resulting fluorescence. The decrease in fluorescence (compared to that before denaturation) is a measure of the rate of DNA denaturation which is directly proportional to the extent of DNA damage. Several factors, particularly the lowered pH at which the denaturation is stopped, have been found important for increased sensitivity. The method is suitable for monitoring the effect on DNA in living cells of environmental factors, drug and radiation therapy, and for toxicology studies. A kit adapted for carrying out the test method is described.

33 Claims, 3 Drawing Figures

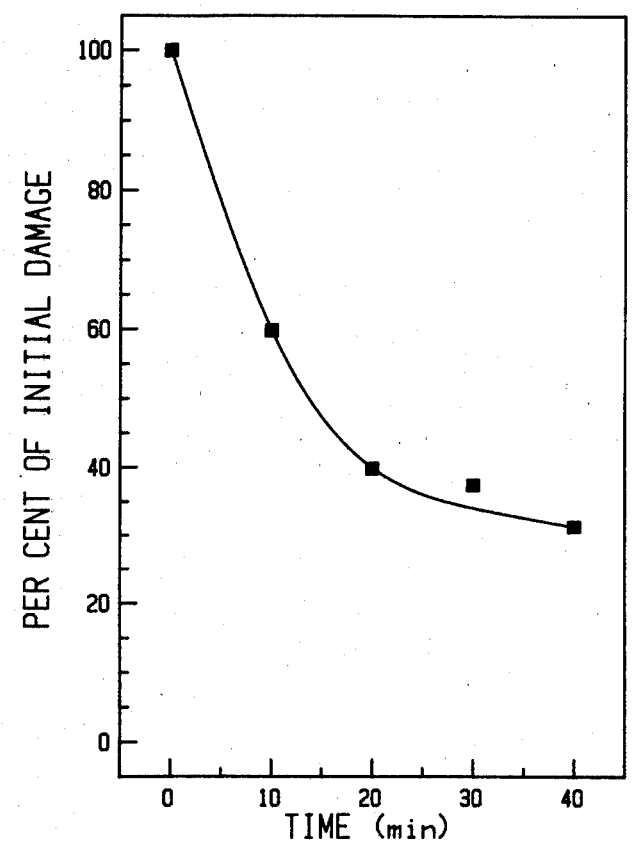

FLUORESCENT DETECTION OF DNA DAMAGE

FIELD OF THE INVENTION

This invention deals with the detection of damage to DNA (deoxytribonucleic acid—the genetic material in nearly all living cells) caused by low doses of radiation, chemicals, or other potentially damaging influences. A sensitive flourescent method has been developed, including a kit for carrying out this assay.

DESCRIPTION OF THE PRIOR ART

DNA is generally considered to be the cellular target in living cells most sensitive to the lethal, mutagenic and carcinogenic effects of radiation, as well as numerous other environmental chemicals and drugs. These agents may damage DNA by altering or disrupting the base or the sugar-phosphate backbone. Although base damage is considered to have more serious consequences for a cell than disruption of the backbone (single-strand breaks), except in the case where both strands are disrupted at positions in close proximity (double-strand breaks), low levels of base damage are difficult to measure by physical or chemical means. In recent years, several methods have been devised for detecting the small number of DNA strand breaks produced by low doses of ionizing radiation ($<1$ Gy) ($1$Gy$=100$ R) or by exposure to certain chemicals. See: G. Ahnström and K. Erixon, Int. J. Radiat. Biol. 23, 285–289, (1973); K. W. Kohn and R. A. G. Ewig, Cancer Res. 33, 1849–1853, (1973); K. W. Kohn, L. C. Erickson, R. A. G. Ewig, and C. A. Friedman, Biochemistry 15, 4629–4637, (1976); B. Rydberg, Radiation Res. 81, 492–495 (1980), Radiation Res. 61, 274–287 (1975); R. B. Sheridan, III, and P. C. Huang, Nucl. Acids Res. 4, 299–318 (1977). In these procedures, intact cells are exposed to alkaline solutions; the rate at which the two strands of the DNA unwind is monitored by separating duplex DNA from single-stranded DNA using either hydroxyapatite chromatography, S1 nuclease digestion, or membrane filtration. The rate of DNA unwinding can then be correlated with the number of strand breaks. These methods have found their greatest use for studying DNA damage in cultured mammalian cells in which the DNA can be labelled with radioactive thymidine.

These methods have been adapted for the study of non-labelled cells by using fluorescent chemicals for quantitating the amount of DNA separated into single-stranded and double-stranded fractions by one of the methods described above. The resultant procedure is rather cumbersome and time-consuming. See: P. H. Gutin, J. Hilton, V. J. Fein, A. E. Allen, and M. D. Walker, Radiation Res. 72, 100–106 (1977); P. M. Kanter and H. S. Schwartz, Analyt. Biochem. 97, 77–84 (1979); and, L. C. Erickson, R. Osieka, N. A. Sharkey, and K. W. Kohn, Analyt. Biochem. 106, 169–174 (1980).

Some fluorescent dyes have the potential for distinguishing between double-stranded and single-stranded DNA directly without the requirement for a physical or enzymatic step in separating the two. Morgan and Pulleyblank were the first to show that, for purified DNA, the fluorescent enhancement of single-stranded DNA is largely abolished at appropriate alkaline pH, with a lesser effect upon the fluorescent enhancement of double-stranded DNA. See A. R. Morgan et al., Nucleic Acids Res., Vol. 7, No. 3, 547–569, 1979.

In addition to the Rydberg and other techniques referred to above, still other methods for detecting DNA strand-breaks in nondividing cells have recently been reported, but they are relatively complex and appear to be less sensitive than is desired for some purposes. See P. R. Cook and I. A. Brazell, Nature 263, 679–682 (1976), and Eur. J. Biochem. 84, 465–477 (1978).

It would be desirable to develop an assay for detecting DNA strand breaks as sensitive as that of Rydberg mentioned above, but simpler and more rapid and without the need of radioisotope labelling or physical and/or chemical means to separate the DNA before quantitation.

THE PRESENT INVENTION

A modified alkaline denaturation assay method has been developed and applied to non-purified DNA from non-dividing, non-cultured cells, such as peripheral blood cells or cells from animal organs. In this method, a selected fluorescent dye is used both to detect double-strand DNA and to monitor its rate of unwinding in alkaline media without the requirement for physical separation of single-stranded from double-stranded DNA. The entire procedure is simple, rapid (less than 3 hours), inexpensive and sensitive (radiation damage from 0.05–0.1 Gy can be detected).

The invention includes a method of measuring the extent of DNA damage in cells which have been exposed to an actual or potential damaging influence, comprising:

(a) partially lysing the cells under test to render the DNA accessible;

(b) incorporating an alkaline reagent, in sufficient amounts to denature DNA, into at least one sample comprising the cell lysate, and allowing DNA strand separation to proceed;

(c) at a chosen point of time during the denaturation period, lowering the pH of each sample to a selected pH sufficiently low to stop the alkaline denaturation, but above that causing any precipitation;

(d) providing that each sample is substantially homogeneous;

(e) adding a fluorescent dye which interacts and fluoresces at the lowered pH with non-denatured double strand DNA but not with single strand DNA or other components, to each sample of lowered pH and measuring the resulting fluorescence; and (f) comparing the fluorescence with that of known undamaged DNA subject to the same denaturation, the amount of any decrease in fluorescence being directly proportional to the extent of DNA damage.

One preferred assay design is to utilize three sets of samples, one set subject to no denaturation, a second set to complete denaturation, and the third set to partial denaturation. From the fluorescence readings of the three sets, the % double-stranded DNA remaining after partial denaturation can be calculated. The % is compared for known undamaged and test (damaged) DNA, the amount of any decrease in the percentage being directly proportional to the extent of DNA damage.

The method is particularly adapted to screen drug, chemical or radiation effects on DNA and to monitor repair of DNA strand breaks, wherein selected DNA-containing cells are exposed to the drug, chemical, or radiation under test, a sample of the exposed cells lysed sufficiently to release DNA, and the DNA treated as in steps (a)–(e).

The invention further includes a kit for quantitatively comparing the extent of damage in DNA molecules due to chemical or radiation influences, comprising in separately packaged units:

(i) lysing reagent which causes partial cell disruption and DNA release;

(ii) alkaline denaturing reagent able to cause separation of the two strands of DNA;

(iii) selected weak acid able to lower the pH due to (ii) only sufficiently to stop DNA denaturation; and (iv) a fluorescent dye which interacts and fluoresces with double-strand DNA but not with single-strand DNA or other cell components at the pH due to (iii). It is possible that the solution (ii) can be derived from (i) plus added alkali (see Examples).

Preferably the kit includes:

(1) a solution at neutral pH capable of supporting cell integrity, and yet not interfere with subsequent alkaline denaturation and/or fluorescence analysis;

(2) a lysing solution, which, when added to cells suspended in (1) causes appreciable cell disruption and DNA release, without interfering with subsequent alkaline denaturation and/or fluorescence analysis;

(3) two alkaline denaturing solutions differing slightly in their densities such that, upon addition to cells in (1+2), diffusion of alkali into the cell lysate is hastened without recourse to a mixing step which could artefactually damage the DNA;

(4) a selected very weak acid solution to lower the pH after the addition of (3) and incubation for an appropriate time, such pH being chosen to avoid precipitation of DNA-protein complexes and allow discrimination between double-stranded DNA and other cell components at a subsequent step;

(5) also desirable is the incorporation of a reducing agent which prevents destruction of the fluorescent dye by an unknown agent found present as a contaminant when blood cells are analyzed;

(6) a fluorescent dye and an appropriate amount of alkali to provide final pH conditions under which the fluorescent dye shows selectivity for double-stranded DNA and not single-stranded DNA or other cell components.

DESCRIPTION OF THE DRAWINGS

FIG. 3 is a graph depicting the decrease in percent of initial radiation damage with incubation time of intact cells at 37° C. (see Example 3), as the intact cells rejoin some of the DNA broken by the radiation.

DETAILED DESCRIPTION AND PREFERRED EMBODIMENTS

Figure 2:
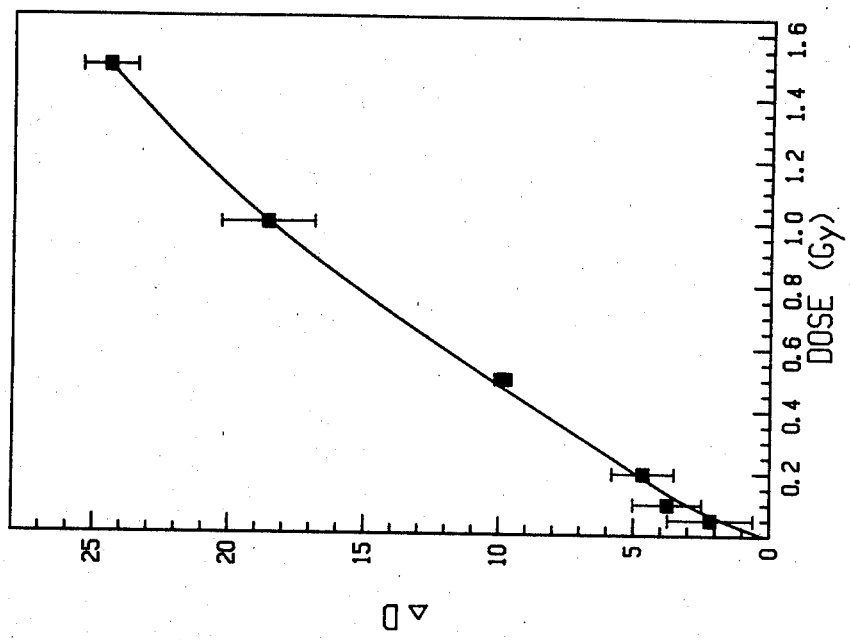
FIG. 2 is a graph of the difference between percentages of double-stranded DNA remaining after 60 minutes of alkaline denaturation at 15° C. versus radiation dose (see Example 2).

The cells can be any lysable cells, with mammalian cells usually being most suitable. Particularly meaningful assays can be obtained with cells from blood or other body fluids, bone marrow, various body organs or tumors.

Intact cells are subjected to the influence believed to damage their DNA, and one or more samples of the exposed cells are separated and readied for test. Before lysing, it has been found desirable to suspend the test cells in a neutral buffer medium containing an osmotic stabilizer. One preferred buffer is sodium phosphate of pH 7-7.5. One stabilizer found to be preferred is inositol with $MgCl_2$. A suitable concentration range for Mg ion is from about 1 to 3 mM, and for inositol is from about 0.2 M to about 0.3 M in the suspending medium (which has been found to minimize cell swelling). Ca ion may be used instead of Mg. Other operative stabilizers include isotonic saline. The cells are suspended in the buffer-stabilizer usually to a concentration of about $5 \times 10^6$ to about $10 \times 10^6$ cells/ml. This preferred buffer-stabilizer combination (phosphate-inositol) has been found to be most advantageous because (i) its contributes little buffering action in pH range 11-13; and (ii) its low salt content minimizes fluorescence quenching later in the method.

After exposure, test cells in suspension are lysed to at least partially release the DNA from protein and other cell components. It has been found desirable to use a mild lysing agent such as urea and a chelator, such as cyclohexanediaminetetraacetate with or without an ionic detergent, particularly sodium dodecylsulfate or sodium lauroylsarcosinate. A suitable final concentration range for urea at cell lysis is from about 3 M to about 5 M in the cell suspension. The sodium dodecylsulfate or equivalent may be present in small amounts, e.g. from about 0.05 to about 0.2%. After sufficient lysis to release the DNA, it is not necessary to separate the cellular debris or otherwise purify the DNA.

The alkaline denaturing reagent used to cause the unwinding or separation of the DNA strands is selected from strong bases of the type of sodium hydroxide and tetrapropylammonium hydroxide. Other operative alkaline reagents include potassium hydroxide, and $NaOH + D_2O$. Sufficient alkaline denaturing reagent should be added to the DNA suspensions to give a pH of about 12 or above, preferably 12.2 to 12.9. Below pH ~11.5 the denaturation substantially ceases. While no significant effect of room light has been found to occur, incubations in the alkaline solutions preferably are carried out in the dark as a precaution for greatest sensitivity.

After a standard denaturation period or at appropriate intervals during the denaturation, samples are treated to lower the pH to a selected value where strand separation ceases but where any precipitation, particularly of DNA-protein complex, is avoided. The selection of pH to avoid any precipitation and to give the most fluorescence has been found important for high sensitivity. In most cases, this lowered pH will be about 11. The use of acids such as acetic or 0.1 N HCl was found to lower the pH to about 10.5 or below and to lead to a precipitation which did not clear reliably on raising the pH to 11.0. Furthermore, these acids provided no buffering capacity at pH 11, which is desirable to maintain this pH. Such precipitation, even in minor amounts, has been found to have a detrimental effect on reproducibility and accuracy of the assay.

An important feature of the invention is the choice of weak acid used to stop the denaturation and avoid precipitation. A very weak acid with buffering capacity at about pH 11 preferably will be used. Glucose has been found most effective in lowering the pH sufficiently to stop the denaturation process (usually about 11), and provides very adequate buffering capacity at this pH. Other very weak acids, less effective than glucose but operative, are fructose, sucrose, lactose, and other soluble sugars.

It is necessary to provide that the samples are substantially homogeneous before proceeding to the fluorescence steps. In most cases, the samples are next subject to a shearing action sufficient to ensure homogenization. One way to carry out a suitable shearing is to pass the solution or suspension through a narrow tube, injection needle, fine tube syringe, capillary, etc. Vibration, e.g. as results from exposure to ultrasound, is another suitable alternative.

When adequate homogenization has been ensured, a selected fluorescent dye is added to each sample and the fluorescence measured in a spectrofluorometer. The dye chosen should interact with double-strand DNA (at pH about 10.5–11.5) rather than single-strand, and show low base-pair specificity. In a preliminary survey, ethidium bromide was found most reliable and is preferred. However, other dyes such as ethidium dimer; 4',6-diamidino-2-phenylindole.2HCl; mithramycin and Hoechst 33258 (2-[2-(4-hydroxyphenyl)-6-benzimidazole]-6-(1-methyl-4-piperazyl)-benzimidazole.3HCl), are expected to be operative at least with some systems.

Features of the method which are desirable for increased sensitivity include steps which minimize, or minimize variability in, (i) the initial dispersion of cells in each sample (a stable uniform dispersions of cells without significant cell clumping is important);

(ii) mixing and handling of the lysate at the time of addition of the alkali (at this stage the system is very sensitive to mixing and localized high concentrations of the alkali); a two-step addition using alkaline solutions of slightly different densities, followed by a period of diffusion at about 0° C., has been found very suitable to ensure the uniform alkaline pH needed with minimal physical mixing;

(iii) precipitation (of chromatin, etc.) upon neutralization of the alkaline solution; the choice of very weak acids with buffering capacity at the lowered pH avoids precipitation by ensuring that the pH does not drop below about 11 even transiently.

In combination these features have been found to give the greatest sensitivity. For example, high sensitivity has been achieved with human peripheral white blood cells, irradiated with $^{60}$Co gamma rays at 0° C. This level of sensitivity achieved can be defined as the detection of as little as about one strand break per chromosome as induced by exposure of human peripheral white blood cells to a very low dose (0.05 Gy) of $^{60}$Co gamma rays.

Practical applications of the method include:

(a) Monitoring cells for DNA damage after accidental exposure of an individual to radiation or carcinogenic chemicals.

(b) Screening of environmental and industrial chemicals for their potential for DNA damage.

(c) Testing of therapeutic agents and drugs (used medically for other purposes) for their potential for DNA damage. Particularly of interest in toxicology since different organs in the body can accumulate drugs to different degrees. Different organs can be examined in experimental animals by this procedure.

(d) Cancer chemotherapy: in vitro testing of cells from an individual to see if they are sensitive to a particular drug. In vivo confirmation, rapidly, of the DNA damaging effect. Detection of the emergence of drug-resistant cell lines as might arise in leukemia. In vivo testing of radiosensitizers.

(e) Laboratory use: for studying basic cellular mechanisms, such as DNA repair and conditions which affect it.

In order to facilitate carrying out the assay, a kit has been provided, as mentioned above. Optionally, the kit may include means to shear the DNA solution such as a fine syringe or an injection needle; and thin-wall disposable glass sample tubes. A reducing agent (to protect the fluorescent dye) may be included alone, or with the weak acid or dye. There may also be included appropriately packaged solutions comprising an osmotic stabilizer, preferably inositol. The packaged units may be appropriate for a single assay or for a series of assays.

The following examples are illustrative. In the solution concentrations, M is molar and mM is millimolar. All % are by weight/volume, unless otherwise indicated. The following aqueous solutions were utilized in at least some of the assays. The solution concentrations and reagents specified have been found very satisfactory and usually will be the most preferred, but are not critical.

(I) A solution of buffered ammonium chloride to facilitate isolation of e.g. peripheral white blood cells, which are a ready source of cellular material for testing. 0.87% NH$_4$Cl/10 mM tris HCl (pH 7.2).

(II) A solution of buffered osmotic stabilizer for suspending isolated cells. 0.25 M meso-inositol/10 mM sodium phosphate/1 mM MgCl$_2$ (pH 7.2).

(III) A solution for lysing cells, inhibiting endogenous nucleases, and freeing DNA from protein. 9 M urea/10 mM NaOH/2.5 mM cyclohexanediaminetetraacetate/0.1% sodium dodecylsulfate.

(IVa) and (IVb) Two alkaline solutions of slightly differing density to provide denaturing conditions for DNA. Use of two solutions of slightly differing density facilitates pH equilibration without the requirement for physical mixing. One is made from 0.40 volume fraction of solution (III) and the second from 0.45 volume fraction of solution (III), both in 0.2 N NaOH.

(V) A solution of very weak acid to lower the pH to 11 and provide buffering capacity thereat. It may include a reducing agent to minimize destruction of the fluorescent dye which can occur if contaminants from blood are present. 1 M glucose/14 mM 2-mercaptoethanol. The reducing agent may be added separately and other equivalent reducing agents may be substituted.

(VI) A fluorescent dye in sufficient alkali to ensure that the final pH will be close to pH 11, at which pH the dye is highly selective for double-stranded DNA. 6.7 $\mu$g/ml ethidium bromide/13.3 mM NaOH. Any of solutions (I) to (VI) would be very suitable for inclusion in a kit (I and II are optional).

EXAMPLE 1

This example illustrates the measurement of the effect of gamma radiation on the kinetics of unwinding (or strand separation) of DNA from non-irradiated and from irradiated human white blood cells.

Blood samples (3 ml) were collected in 5 ml tubes containing 3.6 mM EDTA (ethylenediaminetetraacetic acid) per tube. All tubes except controls were $^{60}$Co gamma-irradiated to 1 Gy (100 rads). The contents of each tube (3 ml) were mixed with 9 ml of solution I (described above). The 12 ml samples were held at 0° C. for 20–30 min. until red cell lysis was complete. The lysate was centrifuged (0° C., 20 min., 400×g), the resulting pellet suspended in 3 ml of the solution I (above) and the cells again centrifuged for 10 min. This second pellet was suspended in 2.7 ml of solution II to give a total white cell concentration of 5–10×10⁶ cells per ml. Aliquots of this suspension (0.2 ml) were placed in tubes and to each tube was added 0.2 ml of solution III and incubated at 0° C. for 10 min. After this incubation, the tubes were divided into three groups for fluorescence measurement of (1) total fluorescence T (primarily double-strand DNA), (2) fully single-strand DNA plus other cell-derived material as background fluorescence B; and (3) partially unwound DNA after alkaline denaturation for a specified period as partial fluorescence P.

For measurement of total fluorescence T, 0.4 ml of solution V was added to the first group, followed by 0.1 ml of solution IVa and 0.1 ml of solution IVb. Samples of this first group were brought to room temperature, sheared by passage through a 22-gauge needle to homogenize, diluted with 1.5 ml of solution VI and their fluorescence read immediately and after 20 min. (Ex 520 nm, An 590 nm). The average of the two sets of readings was used as T.

For measurement of background fluorescence B, 0.1 ml each of solutions IVa and IVb was added and, after 30 min. incubation at 0° C., the alkaline lysate was sheared by passage through a 22-gauge needle, and transferred to a 15° C. bath for the same time period as the third group of samples (below). In all samples of groups (2) and (3), denaturation was stopped by chilling to 0° C. and the addition of 0.4 ml of solution V. After stopping the denaturation, and shearing the samples of this second group, 1.5 ml of solution VI was added and the fluorescence read as before.

To the third group of samples, after the 10 min. incubation at 0° C., was added 0.1 ml of solution IVa and 0.1 ml of solution IVb. This group of samples was further incubated at 0° C. for 30 min., then at 15° C. for the times indicated in FIG. 1. Denaturation was stopped as for the second group, and these alkaline lysate samples sheared by passage three times through a 22-gauge needle. These samples were brought to room temperature, diluted with 1.5 ml of solution VI, and their fluorescence read both immediately and after 20 min., as before. The average of the two readings was used as P.

The percent of double-stranded DNA remaining after the period of alkaline denaturing (D) was calculated as follows for both irradiated and non-irradiated samples:

$$D = \frac{P - B}{T - B} \times 100$$

Figure 1:
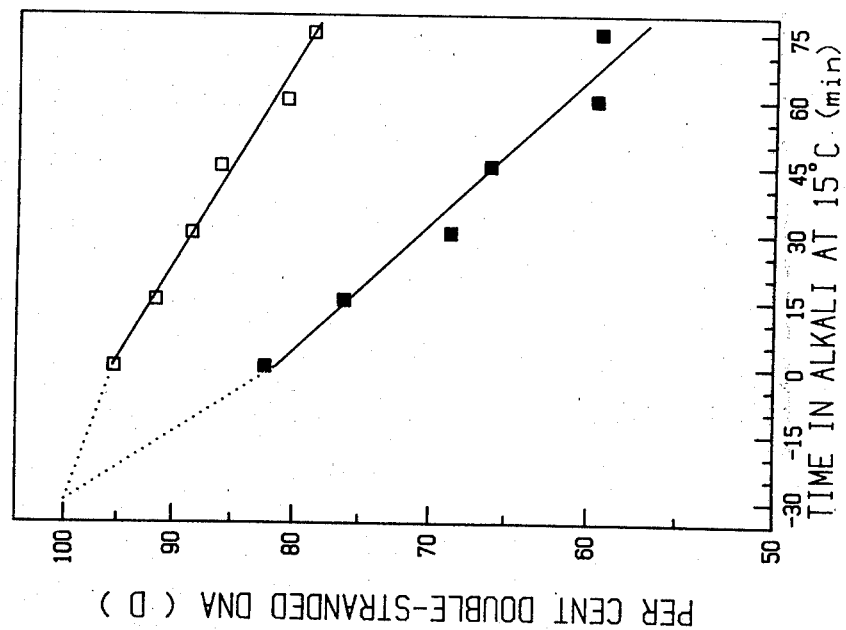
FIG. 1 is a graph showing percent of double-stranded DNA remaining after alkaline denaturation versus time in alkaline denaturing medium, for non-irradiated (-□-) and irradiated (1 Gy of $^{60}$Co γ-rays) (-■-) samples.

Results were plotted (non-irradiated —□— and irradiated —■— to give FIG. 1 from which it is evident that the radiation caused the rate of alkaline denaturing or strand separation to increase, the amount of the increase being a good measure of the extent of DNA damage.

The alkaline buffer system described allowed fluorescence measurements on the DNA complex to be made in crude lysates of cells. The assay procedure provided a relatively good single to noise ratio, that is total fluorescence T was about 2.5 times the background fluorescence B.

EXAMPLE 2

A reproducible dose-response curve for ionizing radiation has been found obtainable by plotting D (measured after 60 min. in alkali at 15° C.) versus dose. Aliquots (3 ml total) of human whole blood were irradiated at 0° C. at dose rates of 0.04–0.16 Gy/min using ⁶⁰Co gamma radiation. Percent residual double-stranded DNA (D) was determined as in Example 1 at 60 min. following transfer of samples to a 15° C. bath. Quadruplicate determinations of D were carried out, and the difference (ΔD) between D values for non-irradiated and irradiated cells was calculated. Values for ΔD were determined in four tests for radiation doses ≦0.2 Gy, and in two tests for doses ≦0.2 Gy. The average values are plotted in FIG. 2. The standard deviations (≦0.2 Gy) or ranges (>0.2 Gy) are shown. These tests emphasize the increase in DNA damage with increase in dose and the ultimate sensitivity of the system in detecting DNA strand breaks.

This assay and resulting dose-response curve can be used as a biochemical dosimeter, i.e. one way of assessing the dose to an individual following a radiation accident or radiotherapy (provided a sample of blood was collected and held on ice soon after the exposure).

The time between exposure to radiation or other influence and the assay would be important if strand breaks were repaired rapidly (as they are in cultured cells). The following example illustrates one assessment of the rate of DNA repair in blood cells in vitro.

EXAMPLE 3

Samples of human blood (3 ml) were diluted 1:1 with RPMI Medium 1640 and irradiated (gamma) at 0° C. to a dose of 1 Gy. The irradiated samples were analyzed as in Example 1 either immediately, or after a period of incubation at 37° C. to allow repair of strand breaks in DNA to occur. Values for ΔD were determined as in Example 2, using non-irradiated blood treated in a similar manner. The initial ΔD value (immediately after irradiation) was 17.9%, i.e. in the non-irradiated blood, the % of DNA remaining double-stranded was 81.8%, whereas only 63.9% remained double-stranded in the irradiated sample following 60 min. exposure to alkali. After various incubation times, similar assays were run and a percent of initial damage remaining calculated. Results are plotted in FIG. 3 and indicate that about one half of the damage is repaired in this test system within about 15 min., and about two thirds by 40 min. The initial rate of repair is therefor very rapid; the slower rate after 20 min. may reflect the sub-optimal conditions provided by incubation of diluted blood.

RPMI Medium 1640 is described in Moore et al., J. Amer. Med. Assoc., Vol. 199, p. 519–524, 1967. It is available from Microbiological Associates and other suppliers of such media.

This assay method has application in detecting DNA strand breaks induced in different cell types by other physical and chemical influences, as well as for monitoring subsequent repair. When spleen cells from irradiated mice were examined and assayed, DNA strand breaks were readily measured. Further experiments have shown that this assay readily detected strand breaks induced by chemical agents.

EXAMPLE 4

Samples of human peripheral white blood cells were obtained as in Example 1 and incubated in a simple salt solution at 37° C. for 30 min. with the following agents present, giving the following results. ΔD is a measure of DNA damage, determined as in Examples 1 and 2.

| Agent Added | Concentration | ΔD Observed |
|---|---|---|
| Bleomycin sulfate | 5 μg/ml | 27% |
| Ethylmethanesulfonate | 0.02% v/v | 12% |
| 4-nitroquinoline-N—oxide | $2 \times 10^{-6}$ M | 61% |
| 4-nitroquinoline-N—oxide | $2 \times 10^{-7}$ M | 18% |
| Stannous chloride (Sn II) | $5 \times 10^{-5}$ M | 67% |
| $K_2Cr_2O_7$ (Cr VI) | $5 \times 10^{-5}$ M | 12% |

These assays confirm that these added agents are genotoxins. For the 4-nitroquinoline-N-oxide at $2 \times 10^{-7}$ M, this low concentration is within a biologically-significant range for cultured mammalian cells, i.e. 10-20% survival. With other assays such as by sedimentation, detecting the effect at even higher concentrations of $5-10 \times 10^{-6}$ M is very difficult: thus the present assay has considerable sensitivity. (See P. J. Smith et al, Nature, Vol. 287, 747-749, 1980.)

I claim:

1. A method of measuring the extent of DNA damage in living cells which have been exposed to an actual or potential damaging influence, without purifying the DNA, comprising:
   (a) partially lysing the cells under test to render the DNA accessible;
   (b) incorporating an alkaline reagent, in sufficient amounts to denature DNA, into at least one sample comprising the cell lysate, and allowing the DNA strand separation to proceed;
   (c) at a chosen point of time during the denaturation period when the difference in amounts of double-stranded DNA between damaged and undamaged DNA is large, lowering the pH of each sample to a selected pH sufficiently low to stop the alkaline denaturation, but above that causing any precipitation;
   (d) providing that each sample is substantially homogeneous;
   (e) adding a fluorescent dye which interacts and fluoresces at the lowered pH with non-denatured double stand DNA but not with single strand DNA or other cell components, to each homogeneous sample of lowered pH containing DNA, denatured DNA and other cell components, and measuring the resulting fluorescence; and
   (f) comparing the fluorescence with that of known undamaged DNA subject to the same denaturation, the amount of any decrease in fluorescence being directly proportional to the extent of DNA damage.

2. The method of claim 1 wherein the cells are partially lysed in the presence of urea.

3. The method of claim 1 wherein mixtures of different types of cells, before lysis (a), are suspended uniformly in ammonium chloride solution causing lysis of some of the cell types, and specific unlysed cells isolated for subsequent lysis in (a).

4. The method of claim 1 wherein isolated cells are suspended in an osmotic stabilizer solution.

5. The method of claim 4 wherein the osmotic stabilizer comprises inositol, buffer and divalent Mg or Ca ions.

6. The method of claim 1 wherein the cells are blood or other body fluid, bone marrow, tumor or tissue cells including selected body organ cells.

7. The method of claim 1 wherein the alkaline denaturing reagent is selected from strong bases of the type of sodium or potassium hydroxide and tetrapropylammonium hydroxide.

8. The method of claim 7 wherein alkaline solutions of different densities are added to facilitate obtaining pH equilibrium.

9. The method of claim 7 wherein the alkaline denaturing step (b) takes place at a pH of about 12 or above.

10. The method of claim 9 wherein the pH is within 12.2 to 12.9.

11. The method of claim 1 wherein the denaturing is stopped in step (c) by lowering the pH to about 11 and substantially no further.

12. The method of claim 11 wherein the pH is lowered by adding a soluble sugar.

13. The method of claim 12 wherein the sugar is glucose.

14. The method of claim 1 wherein a reducing agent protective for the dye is present in step (e).

15. The method of claim 1 wherein in step (d) a shearing action is provided.

16. The method of claim 1 wherein the dye is ethidium bromide.

17. The method of claim 1 adapted to screen drug, chemical or radiation effects on DNA and to monitor repair of DNA strand breaks, wherein selected DNA-containing cells are exposed to the drug, chemical or radiation, a sample of the exposed cells lysed sufficiently to release DNA, and the DNA treated and assayed as in steps (b)-(f).

18. The method of claim 1 wherein blood under test is dispersed in ammonium chloride solution and incubated until red cell lysis is complete, the lysate centrifuged to separate white cells, the white cells suspended in meso-inositol-sodium phosphate-$MgCl_2$ solution, partially lysed in step (a) with added urea-NaOH-Na dodecylsulfate solution, the released DNA subject to alkaline denaturation in step (b) with added alkaline reagent to pH 12.2-12.9, the denaturation stopped in step (c) by adding glucose to about pH 11, ethidium bromide added in step (e) and the fluorescence measured at about pH 11.

19. A kit for quantitatively comparing the extent of damage in DNA molecules due to chemical or radiation influences, comprising, in separately packed units;
   (i) lysing reagent which causes partial cell disruption and DNA release;
   (ii) alkaline denaturing reagent able to cause separation of the two strands of DNA released by (i);
   (iii) a selected very weak acid sugar able to lower the pH due to (ii) sufficiently to stop DNA denaturation yet insufficient to permit precipitation and able to provide buffering capacity at about pH 11; and
   (iv) a fluorescent dye which interacts and fluoresces with double-strand DNA but not with single-strand DNA or other cell components at the pH due to (iii) wherein the lysing reagent, the alkaline denaturing reagent, the sugar acid and fluorescent dye are present in amounts sufficient to perform the assay of claim 1.

20. The kit of claim 19 including physical means to shear and homogenize the DNA solution.

21. The kit of claim 20 wherein said shear means comprises a fine needle.

22. The kit of claim 19 wherein lysing reagent includes urea.

23. The kit of claim 22 wherein the lysing reagent includes an ionic detergent.

24. The kit of claim 19 wherein the alkaline denaturing reagent (ii) is selected from the group consisting of sodium or potassium hydroxide, tetrapropylammonium hydroxide and $NaOH + D_2O$ where $D_2O$ is the solvent.

25. The kit of claim 19 wherein the sugar comprises glucose.

26. The kit of claim 19 wherein the fluorescent dye (iv) comprises ethidium bromide.

27. The kit of claim 19 including a solution of an osmotic stabilizer for suspending isolated cells from which DNA is to be released.

28. The kit of claim 27 wherein the stabilizer solution includes inositol.

29. The kit of claim 19 including buffered ammonium chloride solution.

30. The kit of claim 19 wherein the denaturing reagent (ii) is in the form of two alkaline solutions of slightly differing densities selected to facilitate diffusion without mixing which would damage DNA.

31. The kit of claim 19 including a reducing agent to minimize destruction of the fluorescent dye in the presence of contaminants from blood.

32. The kit of claim 26 wherein the ethidium bromide is utilized in an alkaline solution.

33. The kit of claim 19 comprising:
(I) a solution of ammonium chloride buffered near neutral pH;
(II) a solution of meso-inositol, sodium phosphate and $MgCl_2$;
(III) a solution comprising urea, NaOH, cyclohexanediaminetetraacetate and Na dodecylsulfate;
(IVa) and (IVb) two alkaline solutions comprising sodium hydroxide of slightly different densities;
(V) a solution comprising glucose; and
(VI) a fluorescent dye solution at pH about 11 and comprising ethidium bromide.

* * * * *